(12) United States Patent
Yoshida et al.

(10) Patent No.: US 8,106,009 B2
(45) Date of Patent: Jan. 31, 2012

(54) PHARMACEUTICAL COMPOSITION FOR PREVENTING OR TREATING ISCHEMIC DISEASES

(75) Inventors: Yoshihiro Yoshida, Kagoshima (JP); Shinya Ikematsu, Kanagawa (JP); Sadatoshi Sakuma, Kanagawa (JP); Munehiro Oda, Kanagawa (JP)

(73) Assignee: Medical Therapies Limited, Sydney (AU)

( * ) Notice: Subject to any disclaimer, the term of this patent is extended or adjusted under 35 U.S.C. 154(b) by 622 days.

(21) Appl. No.: 10/371,030

(22) Filed: Feb. 21, 2003

(65) Prior Publication Data

US 2004/0219129 A1 Nov. 4, 2004

Related U.S. Application Data

(63) Continuation of application No. 09/509,332, filed on Jul. 3, 2000, now abandoned.

(30) Foreign Application Priority Data

Sep. 26, 1997 (JP) .................................. 9-279435

(51) Int. Cl.
*A61K 38/18* (2006.01)
*C07K 14/475* (2006.01)
(52) U.S. Cl. .................. 514/8.3; 514/17.7; 530/350
(58) Field of Classification Search .................. None
See application file for complete search history.

(56) References Cited

U.S. PATENT DOCUMENTS

| | | | |
|---|---|---|---|
| 5,210,026 A | 5/1993 | Kovesdi | |
| 5,629,284 A | 5/1997 | Unoki et al. | |
| 5,670,477 A * | 9/1997 | Poduslo et al. | 514/2 |
| 5,702,372 A * | 12/1997 | Nelson | 604/264 |
| 5,733,871 A * | 3/1998 | Alps et al. | 514/12 |
| 6,083,907 A | 7/2000 | Uchida | |
| 2003/0202960 A1* | 10/2003 | Colley | 424/85.1 |
| 2004/0077579 A1 | 4/2004 | Kadomatsu et al. | |

FOREIGN PATENT DOCUMENTS

| | | |
|---|---|---|
| JP | 8027021 | 1/1996 |
| JP | 8073498 A | 3/1996 |
| WO | WO 98/40095 | 9/1998 |

OTHER PUBLICATIONS

Yoshida et al. Intraventricular administration of the neurotrophic factor midkine ameliorates hippocampal delayed neuronal death following transient forebrain ischemia in gerbils. Brain Res. Mar. 9, 2001;894(1):46-55.*
Abe et al. Protective role of nerve growth factor against postischemic dysfunction of sympathetic coronary innervation. Circulation. Jan. 7, 1997;95(1):213-20.*
Tomomura et al. A retinoic acid-responsive gene, MK, found in the teratocarcinoma system. Heterogeneity of the transcript and the nature of the translation product. J Biol Chem. Jun. 25, 1990a;265(18):10765-70.*
GenBank Database Accession No. J05473, National Center for Biotechnology Information, Bethesda, MD. Apr. 27, 1993.*
English translation of JP 8-27021, Translated: 09:39:26 JST Jan. 18, 2011.*
Iwashita, Nobuhiko et al., "Expression of Midkine in Wound Healing (In Japanese)", *The Journal of Japanese Biochemical Industry*, 1996, 68(7):849.
Kadomatsu, K. et al., "cDNA Cloning and Sequencing of a New Gene Intensely Expressed in Early Differentiation Stages of Embryonal Carcinoma Cells and in Mid-Gestation Period of Mouse Embryogenesis", *Biochem. Biophys. Res. Commun.*, Mar. 30, 1988, 151(3):1312-1318.
Matsuda, S. et al., "Interleukin-6 prevents ischemia-induced learning disability and neuronal and synaptic loss in gerbils", *Neurosci. Lett.* ,1996, 204:109-112.
Muramatsu, Takashi, "Midkine: Growth/Differetiation Factor Under Retinoic Acid Control (in Japanese)", *The Journal of Japanese Biochemical Industry*, 1994, 66(7):611.
Sano A. et al., "Protection by Prosaposin Against Ischemia-Induced Learning Disability and Neuronal Loss", *Biochem. Biphys. Res. Commun.*, Oct. 28, 1994, 204(2):994-1000.
The Merck Manual, 16th Edition, supervised by Fumimaro Takaku, Yugen Kaisha Medical Book Service, 1995, pp. 483-503, 1397-1402, 1397, 1399, and 1400.
Tomomura, M. et al., "A Retinoic Acid-responsive Gene, MK. Found in the Teratocarcinoma System", *J. Biol. Chem.*, Jun. 25, 1990, 265(18):10765-10770.
Wen, T.-C. et al., "Protective Effect of Basic Fibroblast Growth Factor-Heparin and Neurotoxic Effect of Platelet Factor 4 on Ischemic Neuronal Loss and Learning Disability in Gerbils", *Neurosci.*, 1995, 65(2):513-521.
Wen, T.-C. et al., "Ciliary neurotrophic factor prevents ischemia-induced learning disability and neuronal loss in gerbils", *Neuosc. Lett.*, 1995, 191:55-58.
Tomomura, M. et al., "A Retionoic Acid Responsive Gene, MK, Produces A Secreted Protein With Heparin Binding Activity", Biochem. Biophys. Res. Commun., Sep. 14, 1990, 171(2):603-609.

(Continued)

*Primary Examiner* — David Romeo
(74) *Attorney, Agent, or Firm* — Morrison & Foerster LLP

(57) ABSTRACT

A pharmaceutical composition for treating or preventing cytopathy caused by ischemia, comprising a midkine family protein as an active ingredient, and a pharmaceutical composition for treating or preventing ischemic disorders, comprising a midkine family protein as an active ingredient, are provided. Midkine is efficacious in treating or preventing ischemic disorders and cytopathy caused by ischemia and can remarkably prevent, for example, the development of cerebral infarction, a representative of ischemic brain disorders. The pharmaceutical composition of the present invention is also efficacious against, for example, cerebral ischemic disorders such as cerebrovascular-spasm following a subarachnoid hemorrhage, Alzheimer's disease, senile dementia of Alzheimer's type, and cerebrovascular senile dementia, as well as cerebral ischemia, transient cerebral ischemic disease, and head trauma, and other cerebrovascular diseases such as Parkinson's disease, Huntington's chorea, and amyotrophic regressive disorders.

11 Claims, 15 Drawing Sheets

OTHER PUBLICATIONS

Yoshida, Yoshihiro et al., "Expression of MK by Rat Cerebral Infarct and Mouse Cerebral Ischemia (in Japanese)", 1994, *The Journal of Japanese Biochemical Industry* 66(7):688.

Wanaka, Akiko, "Heparinophilic Growth Factor, Neurogenesis and Nerve Injury (in Japanese)", *Advances in Neurological Sciences*, 1994, 38(6):896-904.

Woshida, Y. et al., "Midkine is present in the early stage of cerebral Infract", *Dev. Brain Res.*, 1995, 85:25-30 (abstract discussion, p. 26).

Rauvala, H. et al. "HB-GAM (heparin-binding growth-associated molecule) and heparin-type glycans in the development and plasticity of neuron-target contacts", *Prog. Neurobiol.*, 1997, 62(2):127-144, Oxford.

Muramatsu, Takashi, "Retinoid-responsive Heparin-binding Growth Factor, Midkine (MK) (in Japanese)", *The Journal of Japanese Biochemical Industry*, 65(12):1494-1504.

Merenmies, J. and Heikki Rauvala, "Molecular Cloning of the 18-kDa Growth-associated Protein of Developing Brain", *J. Bio. Chem.*, Oct. 5, 1990, 265(28):16721-16724.

Muramatsu, T., "The Midkine Family of Growth/Differentiation Factor", *Dev. Growth & Differ.*, 1994, 36(1):1-8.

Muramatsu, H. et al., "Midkine, A Retinoic Acid-Inducible Growth/ Differentiation Factor. Immunochemical Evidence for the Function and Distribution", *Dev. Biol.*, 1993,159:392-402.

Michikawa, M. et al., "Retinoic Acid Responsive Gene Product, Midkine, Has Neurotrophic Functions for Mouse Spinal Cord and Dorsal Root Ganglion Neurons in Culture", *J. Neurosci. Res.*, 1993, 35:530-539.

Unoki, K et al., "Rescue of Photoreceptors From the Damaging Effects of Constant Light by Midkine, a Retinoic Acid-Responsivel Gene Product", *Invest. Ophthal. Vis. Sci.*, Nov. 1994, 35(12):4063-4068.

Yoshida, Y. et al., "Midkine is present in the early stage of cerebral infarct", *Dev. Brain Res.*, 1995, 85:25-30.

Obama, H. et al., "Myocardial Infarction Induces Expression of Midkine, a Heparin-Binding Growth Factor with Reparative Activity", *Anticancer Res.*, 1998, 55:145-152.

Kojima, S. et al., "Midkine Enhances Fibrinolytic Activity of Bovine Endothelial Cells", *J. Biol. Chem.*, Apr. 21, 1995, 270(16):9590-9596.

Nakagaware, A. et al., "Differential Expression of Pleiotrophin and Midkine in Advanced Neuroblastomas", *Cancer Res.*, Apr. 15, 1995, 55:1792-1797.

Aridome, K. et al., "Increased Midkine Gene Expression in Human Gastrointestinal Cancers", *Jpn. J. Cancer Res.*, Jul. 1995, 86:855-661.

Takeda, A. et al., "Induction of Heparin-Binding Growth-Associated Molecule Expression in Reactive Astrocytes Following Hippocampal Neuronal Injury", *Neurosci.*, 1995, 68(1):57-64.

Frautschy, S.A. et al., "Localization of basic fibroblast growth factor and its mRNA after CNS Injury", *Brain Res.*, 1991, 553:291-299.

Haynes, L.W., "Fibroblast (Heparin-Binding) Growing Factors in Neuronal Development and Repair", *Mol. Neurobiol.*, 1988, 2:263-289.

Takaaki, Kirino, "Delayed Neuronal Death in the Gerbil Hippocampus Following Ischemia", *Brain Res.*, 1982, 239:57-69.

Mitani, A. et al., "Transient forebrain ischemia of three-minute duration consistently induces severe neuronal damage in field CA1 of the hippocampus in the normothermic gerbil", *Neurosci. Lett.*,1991, 131:171-174.

Araki, H. et al., "Behavioral, Electroencephalographic and Histopathological Studies on Mongolian Gerbils With Occluded Common Carotid Arteries", *Physiol. Behavior*, 1986, 38:89-94.

Speir, E. et al.,"Acidic and Basic Fibroblast Growth Factors in Adult Rat Heart Myocytes", *Circulation Res.*, Aug. 1992, 71(2):251-259.

Mitsiadis, T.A. et al., "Midkine (MK), a Heparin-binding Growth/ Differentiation Factor, Is Regulated by Retinoic Acid and Epithelial-Mesenchymal Interactions in the Developing Mouse Tooth, and Affects Cell Proliferation and Morphogenesis", *J. Cell Biol.*, Apr. 1, 1995, 129(1):267-281.

Muramatsu, H. et al., "Localization of Heparin-Binding Neurite Outgrowth and Antigenic Regions in Midkine Molecule", *Biochem. Biophys. Res. Commun.*, Sep. 15, 1994, 203(2):1131-1139.

Kojima, S. et al., "Synthetic Peptides Derived From Midkine Enhance Plasminogen Activator Activity in Bovine Aortic Endothelial Cells", *Biochem. Biophys. Res. Commun.*, Jan. 17, 1995, 206(2):468-473.

Nakata, N. et al, "Protective effects of basic fibroblast growth factor against hippocampal neuronal damage following cerebral ischemia in the gerbil", *Brain Res.*, 1993, 605:354-356.

Yasuhara, O. et al., "Midkine, A Novel Neurotrophic Factor, is Present in Senile Plaques of Alzheimer Disease", *Biochem. Biophys. Res. Commun.*, Apr. 15, 1993, 192(1):246-251.

Muramatsu T., 1995, BIOSIS Accession No. PREV199598450116.

Muramatsu T., Patent Abstracts of JP8-073498, Jul. 31, 1996, vol. 65 No. 7.

Muramatsu T., 1995, Jpn J Psychopharmacol, vol. 15 No. 3, pp. 275-279.

Yoshida Y. et al., 1995, Journal of Neurochemistry (15th Meeting of the International Society for Neurochemistry), vol. 65 No. Suppl., pp. S114(A) (English Translation attached).

Horiba, M. et al. "Midkine (MK) plays a crucial role in neointimal formation" *J. Amer. Coll. Cardio.*, 1991, 33(2 Supp. A):229A-230A.

Morishita, R. et al. "Intimal hyperplasia after vascular injury is inhibited by antisense cdk 2 kinase oligonucleotides" *J. Clin. Invest.*, 1994, 93:1458-1464.

* cited by examiner

A

B

C

PHARMACEUTICAL COMPOSITION FOR PREVENTING OR TREATING ISCHEMIC DISEASES

CROSS-REFERENCE TO RELATED APPLICATION(S)

This application is a continuation of U.S. Ser. No. 09/509,332, filed Jul. 3, 2000 now abandoned.

TECHNICAL FIELD

This invention relates to a pharmaceutical composition for preventing or treating ischemic diseases with midkine (abbreviated as MK hereinafter) as an active ingredient.

BACKGROUND OF THE INVENTION

Ischemia is a condition wherein the blood flow is completely obstructed or considerably reduced in localized parts of the body, resulting in anoxia, reduced supply of substrates and accumulation of metabolites. Although the extent of ischemia depends on the acuteness of vascular obstruction, its duration, tissue sensitivity to it, and developmental extent of collateral vessels, dysfunction usually occurs in ischemic organs or tissues, and prolonged ischemia results in atrophy, denaturation, and necrosis of affected tissues.

Ischemic cerebrovascular injury development mechanisms are classified into three types, thrombotic, embolic, and hemodynamic. The principal pathological condition for all three types is nevertheless cerebral ischemia, whose severeness and duration define the extent of cerebral tissue injuries. At the site of severe ischemia, nerve and endothelial cells rapidly suffer from irreversible injuries, forming typical infarction nidi due to necrosis. Although the bloodstream moderately declines and functions of neurocytes are suspended in the ischemic penumbra, their survival capacity is not lost and the remaining cerebrovascular system can recover its functions when circulation is resumed via collateral vessels.

In ischemic cardiopathy, which are diseases that affect the coronary artery and cause myocardial ischemia, the extent of ischemic myocardial cell injury proceeds from reversible cell damage to irreversible cell damage with increasing time of the coronary artery obstruction.

Drugs for preventing such cytopathy caused by ischemia or stimulating the regeneration of damaged cells may conceivably provide fundamental therapy of ischemic cerebral and cardiac disorders.

Based on this concept, drugs efficacious in preventing and treating neurocyte injury following the transient cerebral ischemia have been reportedly screened by injecting candidate substances for ischemic brain protective factors into the ventricle or peripheral blood vessel and studying the effect of the substances morphologically and functionally. For example, the intraventricular administration of prosaposin to Mongolian gerbils significantly relieved learning disability after ischemia, and pathological inspection of the hippocampal CA1 area revealed a remarkable increase of the number of pyramidal cells compared with the control (Sand, A. et al.: Biochem. Biophys. Res. Commun. 204: 994-1000, 1994). Like prosaposin, it has been proven that the intraventricular injection of ciliary neurotropic factor (CNTF) and interleukin-6 (IL-6) also significantly increased, in a dose-dependent manner, the number of pyramidal cells and synapses in the CA1 area (Wen, T-C et al.: Neurosci. Lett. 191: 55-58, 1995) (Matsuda, S. et al.: Neurosci. Lett. 204: 109-112, 1996). The intraventricular injection of basic fibroblast growth factor (bFGF) has also been reported to significantly protect against ischemic hippocampus, though not in the same way as prosaposin, CNTF and IL-6 (Wen, T-C et al.: Neuroscience, 65: 513-521, 1995). However, action mechanisms of these protective factors for ischemic brain disorders have not been clarified in detail.

DISCLOSURE OF THE INVENTION

The present invention provides a novel pharmaceutical composition for treating or preventing various diseases caused by cell death due to ischemia or stress, which comprises a midkine (MK) family protein as an active ingredient.

More specifically, this invention provides: (1) a pharmaceutical composition for treating or preventing cytopathy caused by ischemia or stress, comprising a midkine (MK) family protein as an active ingredient; (2) the pharmaceutical composition according to (1), wherein said cytopathy caused by ischemia or stress occurs in brain parenchyma, (3) the pharmaceutical composition according to (2), wherein said brain parenchyma is pyramidal cells in the hippocampal CA1 area; (4) a pharmaceutical composition for treating or preventing diseases caused by cytopathy due to ischemia or stress, comprising a midkine (MK) family protein as an active ingredient, (5) the pharmaceutical composition according to (4), wherein said disease due to ischemia is cerebral infarction, and (6) the pharmaceutical composition according to (4), wherein said disease due to ischemia is myocardial infarction.

Midkine (MK) is a heparin-binding secretory protein abundant in basic amino acids and cysteine. It was discovered as the product of a gene that was transiently expressed in the differentiation process of embryonic tumor cells induced by retinoic acid (Kadomatsu, K. et al.; Biochem. Biophys. Res. Commun. 151: 1312-1318, 1988; Tomomura, M. et al.: J. Biol. Chem. 265: 10765-10770, 1990; Tomomura, M. et al.: Biochem. Biophys. Res. Commun. 171: 603, 1990). MK shares 45% homology with pleiotrophin (PTN) discovered later (Merenimies, J. & Rauvala, H.: J. Biol. Chem. 265: 16721-16724, 1990), and MK and PTN thus form the MK family (Muramatsu, T.: Dev. Growth Differ., 36: 1-8, 1994).

Many data on the function of MK have been accumulated, and its more novel important functions are now very likely to be discovered. Principal functions of MK include the following five functions: 1) neurotrophic factor activity (MK stimulates the survival and neurite outgrowth of neurocytes (Muramatsu, H. et al.: Dev. Biol., 159: 392, 1993; Hichikawa, M. et al.: J. Neurosci. Res. 35: 530, 1993; Kikuchi, S. et. al., 160, 1993)); 2) wound healing (MK alleviates and prevents retinal denaturation due to the prolonged irradiation by white light (Unoki, K. et al.: Ophthalmol. Vis. Sci., 35: 4063, 1994) and expression of MK is induced near infarct nidi in the early stage of experimental cerebral and myocardial infarctions in rats (Yoshida, Y. et al.: Dev. Brain Res., 85; 25-30, 1995; Obama, H. et al. Anticancer Research, 18: 145-152, 1998)); 3) ontogenesis (MK is transiently expressed with a peak in the embryonal mid stage, and accumulates mostly in the kidney in the late stage); 4) activation of fibrinolytic system (MK increases three- to five-fold the plasminogen activator activity of vascular endothelial cells derived from bovine aorta at a concentration of 10 ng/ml (Kojima, S. et al.: J. Biol. Chem., 270: 9590, 1995)); and 5) cancer (MK is expressed in a high frequency in Wilms' tumor, breast cancer, lung cancer, neuroblastoma, esophagus cancer, stomach cancer, colon cancer, and hepatoma (Tsutsui, J. et al.: Cancer Res., 53: 1291, 1933; Garver, R. I., et al.: Cancer, 74: 1584, 1994; Garver, R. I., et al.: Am. J. Respir. Cell Mol. Biol., 9: 463, 1993; Nakagawa, A. et al.: Cancer Res., 55: 1792, 1995; Aridome, R. et al.: Jpn. Cancer Res., 86: 655, 1995).

As described above, the expression of MK is induced near infarct nidi in the early stage after the experimental cerebral infarction in rats, and it has been demonstrated that it was expressed exclusively in astrocytes (Yoshida, A., et al.: Dev. Brain Res., 85:25-30,1995). PTN, which forms the family together with MK, is also strongly expressed in the hippocampus, mainly in the CA1 area, and mostly in astrocytes, of rat on the fourth day after development of the transient ischemia in the rat forebrain (Takeda, A. et al.: Neuroscience, 68: 57-64, 1995). Conventionally, the activation of astrocytes that accompanies ischemia has been understood to protect cells. MK and PTN may play a role in the repair process of central nervous system after development of ischemia.

The present inventors assumed that MK might be transiently expressed in human patients with cerebral infarction after onset of the disorder and determined MK concentrations in sera from 150 healthy individuals and 36 cerebral infarction patients. The average serum concentration of MK in healthy individuals was found to be 0.3 ng/ml compared with 0.9 ng/ml in patients. Furthermore, MK concentrations tended to be higher in the serum samples collected from the patients right after development of the disorder and from patients having greater infarction areas. These phenomena are assumed to be due to the circulation of MK transiently expressed near the ischemic region.

Recently, increased expression of various neurotrophic is factors in nerve injuries caused by trauma, ischemia, etc. has been reported (Frautschy, S. A. et al.: Brain Res., 553: 291, 1991; Haynes, L. W.: Neurobiol., 2: 263, 1988). These neurotrophic factors are probably involved in repair mechanisms of nerve injuries and act on neurocytes either directly or indirectly via gliacytes to play important roles in their survival and repair.

Based on these reports, the present inventors examined whether MK is involved in mechanisms of repairing nerve injuries like other neurotrophic factors using an experimental model of cerebral ischemia. MK was intraventricularly injected into Mongolian gerbils, one such model, before and after the operation to develop ischemia in order to morphologically examine suppressive effects of MK on deciduation of hippocampal CA1 neurons. Since the anastomosis of internal carotid artery and vertebral artery systems in Mongolian gerbils, retracts after the age of eight weeks, an excellent model of incomplete forebrain ischemia can be readily prepared by obstructing the bilateral common carotid arteries with clips for three to five minutes so that a certain denaturation of neurocytes (delayed neurocyte death) is caused in a specific site (hippocampal CA1 area) in 48 to 72 hours by reperfusion following ischemia. Therefore, a transient forebrain ischemia model of Mongolian gerbils is useful for assessing protective factors for ischemic brain (Kirino, T. et al.: Brain Res. 237: 57-69, 1982; Mitani, A. et al.: Neurosci. Lett. 131: 171-174, 1991).

MK was intraventricularly injected into Mongolian gerbils prior to the ischemic operation to examine its protective effects on ischemic brain. A 2-mm-deep hole was made 2 mm from the bregma of a Mongolian gerbil, and physiological saline containing MK (0.063, 0.125, 0.25, 0.5, 1.0 and 2.0 µg), PTN (0.5, 1.0 and 2.0 µg), or, for comparison, bFGF (1.0 and 2.0 µg), which is known to have protective effects on the ischemic brain, was intraventricularly injected into the animals. After four minutes, the bilateral common carotid arteries were ligated to obstruct the circulation for five minutes so that a transient ischemic forebrain model was prepared. Ninety-six hours or seven days after the circulation was resumed, the brain was excised and fixed under perfusion with 4% paraformaldehyde. From the paraffin block thus prepared, 5-µm thick sections were prepared and stained with hematoxylin-eosin to count the number of viable neurocytes per 1 mm of the left hippocampal CA1 area. As shown in Tables 1 and 2, deciduation of hippocampal CA1 neurocytes was significantly suppressed in the MK (0.5 µg or more) administered group and in the PTN (2.0 µg or more) administered group as compared with the control group (injected with physiological saline).

bFGF significantly suppressed deciduation of hippocampal CA1 neurocytes at a concentration of 2.0 µg or more as compared with the control group. These results indicate that the previous administration of MK or PTN into the ventricle can suppress (prevent) brain cell injury caused by ischemia and the subsequent perfusion.

In addition, MK was intraventricularly administered to Mongolian gerbils after the ischemic operation to examine its protective effects on ischemic brain. After the transient forebrain ischemia was constructed in the same manner as described above, blood circulation was resumed, and 48 hours later MK was intraventricularly injected in the same manner as above. On day seven after the injection, 5-µm thick sections were prepared similarly as described above and stained with hematoxylin-eosin to count the number of viable neurocytes per millimeter of the area of the left hippocampal CA1 neurocytes. About 160 viable neurocytes per mm of hippocampus were observed (Example 1.2). This number of viable cells is about the same as that when 0.5 µg of MK was administered just prior to the ischemic operation.

High-level mentation such as memory or learning is definitely the basis of mental activity in humans. Therefore, the development of drugs capable of reducing hindrances to memory and learning has become one of the most interesting tasks in neuroscience. Many experimental models of memory or learning hindrance are known, and test methods thereof are extremely various. One such test, the passive avoidance learning test, is frequently used with mice.

In arriving at this invention, the present inventors clarified that intraventricular administration of MK or PTN within a certain period before or after a transient forebrain ischemia operation significantly suppresses deciduation of hippocampal CA1 neurocytes as compared with control. Furthermore, the number of hippocampal neurocytes reportedly correlates well with the improvement of response lag time in the step-down type passive avoidance learning test (Araki, H. et al.: Physiol. Behav. 38: 89-94, 1986; Sano, A. et al.: Biochem. Biophys. Res. Commun. 204: 994-1000; Wen, T.-C. et al.: Neuroscience, 65: 513-521; Wen, T.-C. et al.: Neurosci. Lett. 191: 55-58). Therefore, the response lag time can be improved by intraventricular injection of MK or PTN before or after ischemic loading. The fact that hippocampal CA1 neurocytes are most easily injured by cerebral ischemia and the subsequent perfusion, the experimental results that the deciduation of hippocampal CA1 neurocytes in animal groups injected with K or PTN before or after ischemia was significantly suppressed as compared with control groups, and the report suggesting that MK or PTN improves the response lag time in the step-down type passive avoidance learning test all indicate that MK or PTN can be expected to be useful both for preventing and treating neurocyte injury caused by cerebral ischemia and subsequent perfusion and for improving mental disorders, which is the ultimate purpose of these remedies.

In addition, Example 3 below reveals that, in the case of nerve cell injury caused by both ischemic stresses and other stresses such as traumatic stress, MR, in response to the early stage of such injury, is expressed near the injured sites.

Therefore, MK or PTN can be used to prevent or treat various cranial nerve disorders by directly preventing the dysfunction, denaturation and cell death of neurocytes in overall or specific regions from fundamental causes such as ischemia, trauma and aging or no accountable causes, and by stimulating the regeneration of injured neurocytes. In addition, using MK combined with other neurotrophic factors such as bFGF having different action mechanisms may produce synergistic or additive protective effects to prevent neurocyte death caused by ischemia or stress. Specific disorders to be treated may include cerebral infarction, transient cerebral ischemia, encephalopathy due to the cerebrovascular spasm such as sequela of subarachnoid hemorrhage, senile dementia, and encephalopathy at the time of anabiosis following cardiac arrest.

The present inventors also constructed an experimental cardiac infarction model by ligating the left descending coronary artery of rat to detect the MK expression in cardiac cells by immunohistochemical staining (Obama, H., et al.: Anti-cancer Research, 18: 145-152, 1998). The results indicated that the expression of MK was not observed in most of cardiac cells in a normal heart, but was observed in cardiac cells at several places facing the ventricle (FIGS. 4 and 5). In contrast, strong expression of MK was observed in the cardiac infarction model heart on the wall of the right ventricle (RV), the septum, and the endocardium of the wall of the left ventricle facing the right ventricle (LV) (FIG. 6). Other areas on the left ventricular wall corresponding to the cell death region were not stained. Specificity of this MK staining was confirmed because the MK staining disappeared after MK was absorbed by an anti-MK antibody (FIG. 7). Thus, the present inventors immunohistochemically demonstrated the distinct expression of MK in cardiac infarction. Surprisingly, the remarkably intensified MK staining was observed not only in the region adjacent to the infarction site of the left ventricle but also in the entire RV and most areas of the septum (FIG. 6).

Stained and unstained regions are divided by a distinct line that corresponds to the border between coronary artery regions. Interestingly, the expression pattern of MK in a cardiac infarction model differs from that of bFGF in the same model (not shown in the figure).

More detailed examination of MK expression in an infarction model revealed the appearance of MK staining in the RV (FIG. 8) and septum (FIG. 9) (indicated by an arrow and an arrowhead). The septum was extensively magnified, and intense staining was observed at capillaries or the penumbra of myocardial cells facing capillary endothelium (FIG. 10). The interior of myocardial cells is also intensely stained (indicated by asterisk). The stained region was clearly separated from the unstained region by the border between the septum and LV (FIG. 10). AS described above, only a slight and uneven MK staining is observed in LV, except for endomyocardial cells (FIG. 12).

Comparison of mRNA expression in the RV and septum of the infarction model and normal rats by Northern blot analysis revealed that the increased mRNA level is detectable in infarction model rats. In addition to the 1.0 kb MK mRNA, a 1.8 kb band reacting with MK cDNA was detected. This 1.8 kb band might be an isoform of MK mRNA. These results indicate that the increased MK immunoreactivity in the heart shortly after infarction is caused by stable elevation of transcription activity of mRNA.

MK expression is remarkably enhanced in myocardial infarction caused by ligating the left anterior coronary artery (LAD) of a rat. This enhancement is attributed to increased MK mRNA, and is generated in the early stage, within six hours after infarction. In spite of MK expression in a broad area of an infarcted heart, its expression is not detected in regions destined to cell death, indicating that MK is involved in the repair of damaged cardiac tissues.

Considering the fact that, as described above, MK is expressed in the edematous area near necrotic sites shortly after cerebral infarction, the expression of MK indicates its possible participation in the repair or cure process under various pathological conditions. In fact, it has been demonstrated that prior administration of MK prevents the retinal denaturation caused by continuous exposure to light irradiation (Unoki, K., et al., Invest. Ophthalmol. Vis. Sci., 35: 4063-4068, 1994).

bFGF expression is associated with myocardial infarction and has cardioprotective action (Speir, E., et al.: Circ. Res., 71: 215-259, 1992). However, the present inventors could clearly demonstrate that MK was more highly expressed than bFGF under experimental conditions we selected. MK and bFGF jointly increase the plasminogen activator activity in aortic endothelial cells (Kojima, S., et al.: J. Biol. Chem., 270: 9590-9596, 1995). They also enhance proliferation of tooth mesenchymal cells (Mitssiadis, T. A., et al.: J. Cell Biol., 129: 267-281, 1995). Therefore, they may also act in concert in repairing injured cardiac tissues.

In addition, the present inventors have found that MK is also expressed slightly in myocardial cells, and highly expressed in endocardium in normal hearts. This localized expression of MK resembles that of bFGF (Speir, E., et al.: Circ. Res., 71: 215-259, 1992), but their increasing patterns of expression after infarction differ from each other. In normal myocardial cells, bFGF is thought to be involved in promoting DNA synthesis, stimulating survival, retarding aging, and regulating migration and production of extracellular matrix (Speir, E., et al.: Circ. Res., 71: 215-259, 1992). MK might also be playing similar roles in the heart. MK expression after cardiac infraction is enhanced in areas not only proximal but also distal to the infarcted region. This enhanced expression of MK is detected in not only ventricles but also walls of the atria.

From these facts, it is obvious that MK plays important roles in both the generation and repair of the heart, indicating the possibility that abnormality in the expression of MK or signal transduction system may cause various disorders including cardiac disease. Therefore, MK is thought to be useful as a medicament for preventing or treating ischemic cardiac diseases such as myocardial infarction leading to myocardial necrosis due to the obstruction of the coronary artery or acute reduction of blood circulation. Furthermore, MK or PTN can be used as a medicament for preventing or treating a group of other disorders caused by is cytopathy due to ischemia and stress such as ischemic colitis or mesenteric artery occlusion caused by circulation disturbance in the digestive tracts.

MK or PTN of this invention used for treating or preventing disorders due to cytopathy caused by ischemia is preferably a human recombinant MK or PTN, or partial peptide fragments thereof having their biological activities. Native MK is not glycosylated; unglycosylated MK is thus preferable in the present invention. Such MK includes human MK consisting of 121 amino acid residues, but its amino acid sequence is not limited thereto (Muramatsu, T.: Develop. Growth & Differ. 36: 1-8, 1994).

In mouse MK, a signal peptide is cleaved from a precursor protein consisting of 139 amino acid residues to yield the mature MK (consisting of 118 amino acid residues with a molecular weight of 13 kDa). Thirty of these amino acid residues are basic amino acids, and 10 are cysteine residues. Five disulfide linkages formed by the cysteine residues construct two domains at the N- and C-termini. These two domains differ in biochemical and biological properties and may possibly play different roles in in vivo functional expression. The heparin-binding capability is higher on the C-terminus side than the N-terminus side (Muramatsu, H., et al.: Biochem. Biophys. Res. Commun., 203: 1131, 1994). Capabilities for neurite outgrowth and fibrinolysis stimulation are mainly bound in the C-terminus (Muramatsu, H., et al.: Biochem. Biophys. Res. Commun., 203: 1131, 1994; Kojima, S., et al.: Biochem. Biophys. Res. Commun., 206: 468, 1995). Therefore, partial polypeptide fragments having biological activities intrinsic to. MK are also included in this invention.

Specific amino acid(s) in the amino acid sequence of human MK can easily be deleted, inserted, or substituted using recombinant DNA techniques to enhance the activities of the drugs of this invention or improve their safety. For example, amino acid at a specific site can be chemically substituted with its equivalent amino acid. Specifically, a hydrophobic amino acid (such as Ala) can be substituted with both another amino acid (such as Gly) with comparable hydrophobicity and an amino acid with higher hydrophobicity (such as Val, Leu or Ile). Similarly, one negatively charged amino acid residue can be substituted with another amino acid (e.g. replacing Asp with Glu), or one positively charged amino acid residue with another amino acid (e.g. replacing Lys with Arg). In addition, since the C-terminal half of MK, for example, positions 60-121 (C-half 60-121), or positions 62-104 from the C-terminus (C-half 62-104) (Muramatsu, H. et al.: Biochem. Biophys. Res. Commun. 203: 1131-1139, 1994) carries the neurite outgrowth capability and contains the heparin-binding site, they can be useful for drugs of this invention. Also, a hydrophobic amino acid is desirably altered to a charged amino acid as long as such alteration produces no undesirable effect on the biological activity of MK. Those skilled in the art can perform the above modifications so that MK has preferable biological activities. MK and PTN cannot exhibit their efficacy because of the attack from proteinases and interference by unnecessary receptors, like proteinaceous drugs often cannot. Therefore, the stability of MK and PTN in vivo can be elevated by conjugating them with polyethyleneglycol (PEG), polyvinylpyrroridone, dextran, etc. For example, IL-6 hybridized with PEG successfully prolonged the residence of IL-6 in the bloodstream. This invention also includes such chemically modified MK and PTN.

The term "midkine" or "MK" used herein includes all of such modified and altered MKs as long as they retain the original biological activities of MK. The term "MK family" used herein includes all of these modified and altered proteins (MK and PTN) belonging to this family as long as they have biological activities intrinsic to them.

An MK family protein of the present invention can be directly administered to prevent or treat cerebral infarction, myocardial infarction, ischemic colitis, superior mesenteric artery occlusion, etc. Alternatively, it can be formulated into a pharmaceutical composition comprising the active-ingredient by known pharmaceutical preparative methods. For example, it can be formulated into pharmaceutical preparations suitable for effectively administering to human subjects. This includes injection, preparations for nasal inhalation, percutaneous absorption, oral administration, etc., preferably injection. The preparations are administered together with pharmaceutically acceptable carriers or media such as sterilized water, physiological saline, plant oil (e.g. sesame oil, olive oil, etc.), colorant, emulsifier (e.g. cholesterol), dispersant (e.g. gum arabic), surfactant (e.g. polyoxyethylene hydrogenated castor oil surfactant), solubilizer (e.g. sodium phosphate), stabilizer (e.g. sugar, sugar alcohol and albumin), preservative (paraben), etc. Injectable preparations can be provided in the form of lyophilizates, aqueous solution, and products sealed into an osmotic pressure pump. Pharmaceutical preparations of this invention contain MK or PTN, which directly act on the cerebral parenchyma and myocardial cells to exhibit its efficacy. Thus, unlike nosotrophic drugs such as conventionally used cerebral metabolic stimulators and cerebral circulation improving agents, the preparations of this invention can be used to treat various cranial nerve disorders by directly preventing the dysfunction, denaturation and necrosis of neurocytes in overall or specific regions due to fundamental causes such as ischemia, trauma and aging or no accountable causes, and by stimulating the regeneration of injured neurocytes.

The above disorders can be treated by gene therapy by enhancing the expression of MK or PTN protein in ischemically diseased sites using the promoter region of the MK or PTN gene.

The pharmaceutical composition of this invention can be injected, for example, at a daily dose of about 0.001 to 100 µg/kg of MK or PTN protein divided into one to six dosages, intraareterially, intravenously, intramascularly, subcutaneously, intraventricularly, or intraspinally. The composition can also be administered directly into the ventricle and meninx via a catheter inserted therein. Alternatively, it can be incorporated into an osmotic pressure pump and continuously administered via the pump implanted in the body.

It has been reported that the permeability of the blood-brain barrier is transiently elevated by infusing a hypertonic solution of mannitol, urea, etc. via the carotid artery (Proc. Natl. Acad. Sci. USA 76: 481-485, 1979), and that some substances (i.e. alkylglycerol) promote the intracerebral transfer of other drugs. The pharmaceutical composition of this invention can also be administered using these techniques. Furthermore, the possibility of intracerebral uptake of cationized albumin by some mechanisms has been reported (J. Clin. Invest. 70:289-295, 1982). MK or PTN proteins may be administered after they are chemically modified by such a method.

BEST MODE FOR IMPLEMENTING THE INVENTION

Example 1

Figure 1:
FIG. 1 presents photomicrographs (×10) of brain cells two days after being treated with dry ice. A shows the cells in the area infarcted by the dry ice treatment and its vicinity stained with hematoxylin-eosin (H-E staining). B shows an image of an H-E stained, highly injured infarcted area. C shows an image of a similar area to that of B stained with an anti-MK antibody.
Figure 1:
Figure 1:
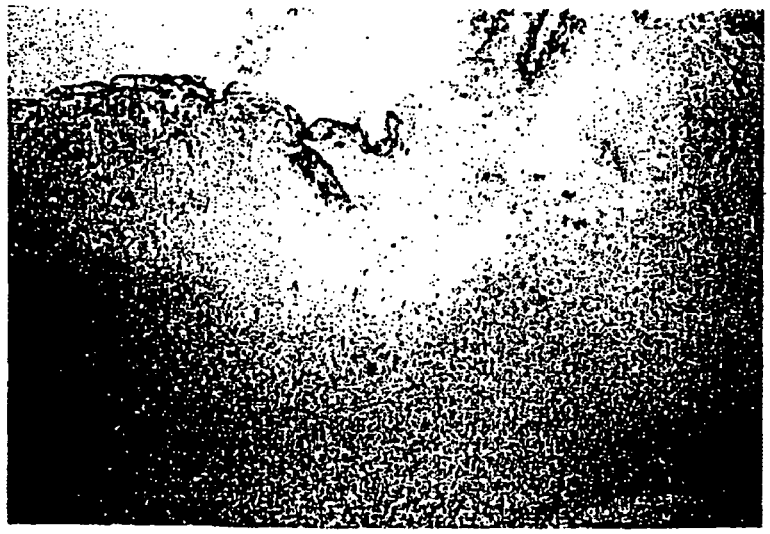

Assessment of Ischemic Brain Protective Substances in a Transient Forebrain Ischemia Model 1.1 Administration of Ischemic Brain Protective Substances Prior to Ischemic Operation
1.1.1 Ischemic Brain Protection by MK Recombinant human MK was prepared according to the method described in Example 1 of Unexamined Published Japanese Patent Application (JP-A) No. Hei 9-95454, and used in Example 1.1.2 and Example 1.2. Six to 16 male Mongolian gerbils (six to eight weeks old, weighing 60 to 80 g) for each group were placed in "HONEY MATIC M-3" (KIMURA MEDICAL INSTRUMENT LTD.), an anesthetic feeding system for fluothane (halothane in Japanese Pharmacopoeia), and anesthetized by appropriately filling the container with an inhalation anesthetic, fluothane. A Mongolian gerbil was fixed onto an operation table equipped with a holder for an insufflator (NARISHIGE SCIENTIFIC INSTRUMENT LAB.: TYPE SR-5N, No. 97024). After the head was subjected to midline incision, a hole for inserting a syringe of an appropriate size was made by a dental drill at 2 mm from the site of bregma toward the left eyeball side.

Through this hole, 2 μL of MK 0.5 mg/mL, 1 mg/mL or 2 mg/mL solution (0.5 μg, 1.0 μg, 2.0 μg) (in physiological saline) was injected into the ventricle with a microsyringe (HAMILTON MICROLITER #701). A saline (Japanese Pharmacopoeia, physiological saline, Otsuka physiological saline injection, Otsuka Pharmaceutical) administered group and the sham operation group (Sham-op) were prepared as control groups. After these solutions were injected into the ventricle, the animals were left for 4 min and the operation site was sutured. The chest was subjected to midline incision to expose both right and left common carotid arteries. Both arteries were ligated with "No. 23 artery Kremmer straight" to stop blood flow for 5 min, after which the blood was permitted to circulate again. During ischemia loading, brain temperature and body temperature were maintained constant (37±0.2° C.). Individual was distinguished and housed in the nursery cage after recovering from anesthesia. The animals were fed and allowed to take water and food freely. After 96 hours, the animals were fixed by perfusing with saline containing 0.2% heparin (Novo Heparin Injection 100; Japan Hoechet Marion Russell, LTD.) and 4% paraformaldehyde solution. The brain was excised from the beheaded head using scissors, and immersed in 4% paraformaldehyde fixative for one day. Tissues containing dorsal hippocampus were dehydrated and penetrated, then embedded in paraffin.

The inventors prepared 5 μm sections, equivalent to 0.5 to 1.0 mm from the tip of the hippocampus or 1.4 to 1.9 mm rear from sagittal suture repared from this paraffin block and stained with hematoxylin-eosin(H-E staining). Using this tissue preparation, the length of hippocampal CA1 was measured five times using a curvimeter one-side type, and the average value thereof was calculated. Pyramidal cells (neurocytes) of the left hippocampus in the hippocampal region were counted under 200-fold magnification, and the result was divided by the above-described average value to calculate the number of viable neurocytes per mm of the hippocampal CA1. The results are shown in Table 1.

TABLE 1

| | Dose (μg) | Number of animals | Number of CA1 neurocyte (cells/mm) ± S.E. |
|---|---|---|---|
| Sham-op group | — | 4 | 237.5 ± 34.59* |
| Physiological saline administered group | — | 6 | 9.6 ± 10.31 |
| MK administered group | 0.5 | 4 | 232.4 ± 17.75* |
| MK administered group | 1.0 | 5 | 221.6 ± 11.04* |
| MK administered group | 2.0 | 4 | 236.2 ± 40.02* |

*p < 0.05 (multiple Dunnett comparison)

As clearly shown in Table 1, MK administered in a single dose of 0.5 μg or more remarkably prevented the delayed neurocyte death in the hippocampal CA1 region.
1.1.2 Comparison of MK's Ischemic Brain Protective Effect with that of Other Ischemic Brain Protective Factors Each ischemic brain protective factor was intraventricularly administered at a dose of 2 μl each. The bilateral common carotid arteries were each ligated using Sugita brain aneurysm clips (standard type; MIZUHO) at two sites. The brain was fixed by perfusion one week later. With exception of these three, modifications, the experiment was performed in the same manner as in 1.1.1. Recombinant human pleiotrophin (PTN) and recombinant human basic fibroblast growth factor (bFGF) were purchased from R & D Systems (Funakoshi). Their doses were 2 μg, 1 μg, and 0.5 μg for PTN, and 2 μg and 1 μg for bFGF. The results are shown in Table 2.

TABLE 2

|  | Dose (μg) | Number of animals | Number of CA1 neurocytes (cells/mm ± S.E.) |
|---|---|---|---|
| Sham-op group | — | 4 | 237.5 ± 34.59 |
| Physiological saline administered group | — | 16 | 15.7 ± 24.43 |
| MK administered group | 0.063 | 6 | 12.6 ± 6.41 |
|  | 0.125 | 10 | 83.4 ± 111.9 |
|  | 0.25 | 15 | 28.3 ± 57.70 |
|  | 0.5 | 6 | 199.5 ± 99.03* |
|  | 1.0 | 8 | 208.5 ± 80.18*** |
|  | 2.0 | 10 | 219.4 ± 73.87*** |
| PTN administered group | 0.5 | 2 | 26.1 ± 4.03 |
|  | 1.0 | 2 | 43.8 ± 0.78 |
|  | 2.0 | 2 | 179.4 ± 33.02* |
| bFGF administered group | 1.0 | 3 | 28.8 ± 28.89 |
|  | 2.0 | 7 | 99.3 ± 74.66* |

*$p < 0.05$,
***$p < 0.001$ (multiple Dunnett comparison)

Also in this example, the dose at which MK exerts statistically significant protective effect on ischemic brain is assumed to be 0.5 μg or more, which is about the same as that obtained in 1.1.1. Although more neurocytes survived at a dose of 0.125 μg than in the physiological saline administered group, the difference was not statistically significant. The dose of PTN required to exert statistically significant protective effect on ischemic brain was approximately 2 μg, which is about four times higher than that of MK. bFGF, which is reportedly effective in protecting an ischemic brain (Nakata, N. et al.: Brain Res., 605: 354-356, 1993), exerted statistically significant protective effect on an ischemic brain at a dos of 2 μg, but the number of viable neurocytes at that dose was less than about half of that obtained at the same dose of MK. From these results, it is evident that MK, as a suppressor for cranial nerve cell death caused by ischemia, shows ischemic brain protective effect in a transient ischemic forebrain model of Mongolian gerbil comparable to that obtained using known ischemic brain protective factors such as prosaposin, ciliary neurotrophic factor (CNTP) or interleukin 6 (IL-6).

1.2 Administration of Ischemic Brain Protective Factors After Predetermined Time of Reperfusion Following Ischemic Operation Except for administering MK 48 hours after reperfusion following an ischemic operation, the experiment was carried out exactly in the same manner as in 1.1.2. When 2 μg MK was administered, the number of viable hippocampal CA1 neurocytes after 48 hours was 160 cells/mm hippocampus. This was approximately equal to the number obtained at a dose of 0.5 μg in 1.1.2. This result revealed that MK administration within a certain time after reperfusion following transient brain ischemia can effectively protect an ischemic brain.

As demonstrated above, the MK family proteins may possibly exert ischemic brain protective effects based on a different action mechanism from that of the known proteinous ischemic brain protective factors. The expression and increase of various neurotrophic factors upon nerve injuries caused by trauma, ischemia, etc. have recently been reported. It is assumed that these neurotrophic factors are involved in repair mechanisms of nerve injury, and act on neurocytes directly or indirectly via gliacytes to play important roles in their survival and restoration. Thus, synergistic or additional effects can be expected by using MK in combination with other neurotrophic factors.

Example 2

Expression of MK in Dry Ice Brain Injury (Cold Injury) Model

Ten male Sprague-Dawley rats (SD rats) (body weight, 160 g) were used. They were anesthetized by intraperitoneal injection of 4% chloral hydrate (10 ml/kg). Scalp was incised with scissors, and dry ice cut into a 7 mm×10 mm piece (about 2-mm thick) was pressed from over the skull for 10 seconds. The scalp was then sutured, and animals were fed again and allowed to take water and food freely. On Days 1, 2, 4, 7, and 14 after the dry ice treatment, two rats were anesthetized by intraperitoneal injection of 4% chloral hydrate (10 ml/kg), and fixed by perfusing physiological saline (Japanese Pharmacopoeia, physiological saline, Otsuka physiological saline injection, Otsuka Pharmaceutical) containing 0.2% heparin (Novo heparin injection 100; Japan Hoechst Marion Roussel) and 4% paraformaldehyde fixative. After being thoroughly fixed, animals were decapitated. Their brains were taken out using scissors and soaked in the 4% paraformaldehyde fixative. After fixation for 24 hours, the sufficiently solidified brain was divided into four pieces from the front end using a double-edged razor (FEATHER). Tissue slices in which the infarcted area could be observed were dehydrated, penetrated, and embedded in paraffin using an automatic embedding machine. From this paraffin block were prepared 5 μm-thick sections. These paraffin slices were subjected to 1) hematoxylin-eosin staining (H-E staining), 2) anti-MK antibody (rabbit anti-mouse MK polyclonal antibody) staining, and 3) apoptosis detection.

FIG. 1 is a photomicrograph (×10) of brain cells two days after the dry ice treatment stained with H-E or anti-MK antibody. A represents infarction nidi produced by dry ice and cells near it, B represents extensively injured infarction nidi, and C represents an area similar to that of B stained with the anti-MK antibody. In C (anti-MK antibody staining), high-level expression of MK is observed near the infarcted area.

Figure 2:
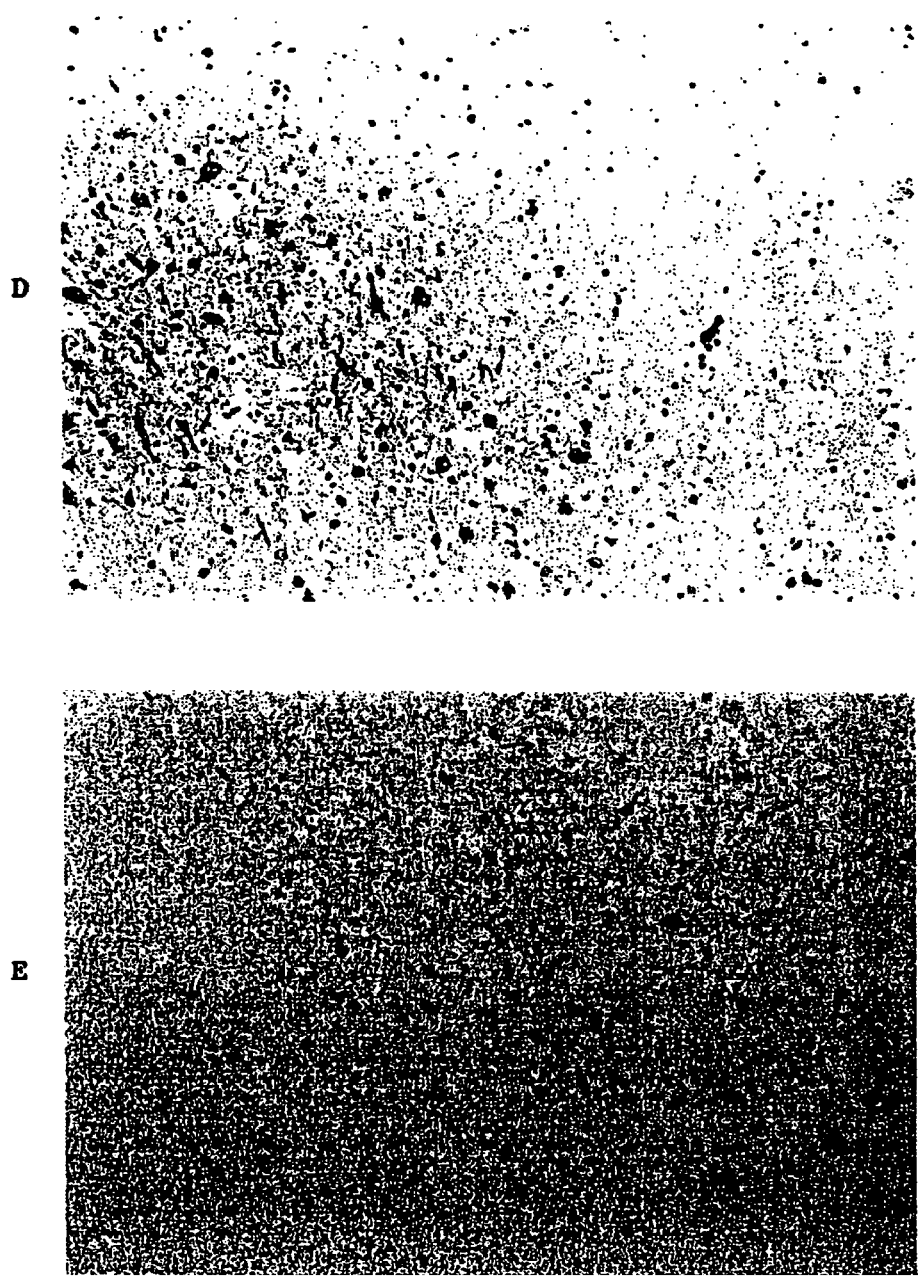
FIG. 2 presents photomicrographs of brain cells two days after being treated with dry ice. D is an enlarged (×50) view of cells near the infarcted area that react with an anti-MK antibody. E shows a similar area to that of D that is apoptosis-stained by the TUNEL method (using a TaKaRa In situ Apoptosis Detection Kit). TUNEL reaction-positive cells resulting in apoptosis following the fragmentation of nucleus are observed.

FIG. 2 is a photomicrograph (×10) of brain cells two days after the dry ice treatment stained with the anti-MK antibody or stained for detection of apoptosis. D represents an enlarged (×50) view of cells near the infarcted area that reacted with the anti-MK antibody. E represents a photomicrograph of cells near the infarcted area similar to D that were examined by the TUNEL method (using a TaKaRa In situ Apoptosis Detection Kit) to determine whether they caused apoptosis. Cells with nuclear fragmentation and positive to TUNEL reaction can be detected. As shown in FIG. 2, the more faintly the infarction nidi were stained, the higher damage the cells received.

Example 3

Expression of MK in Rat Brain Injury Model

Figure 3:
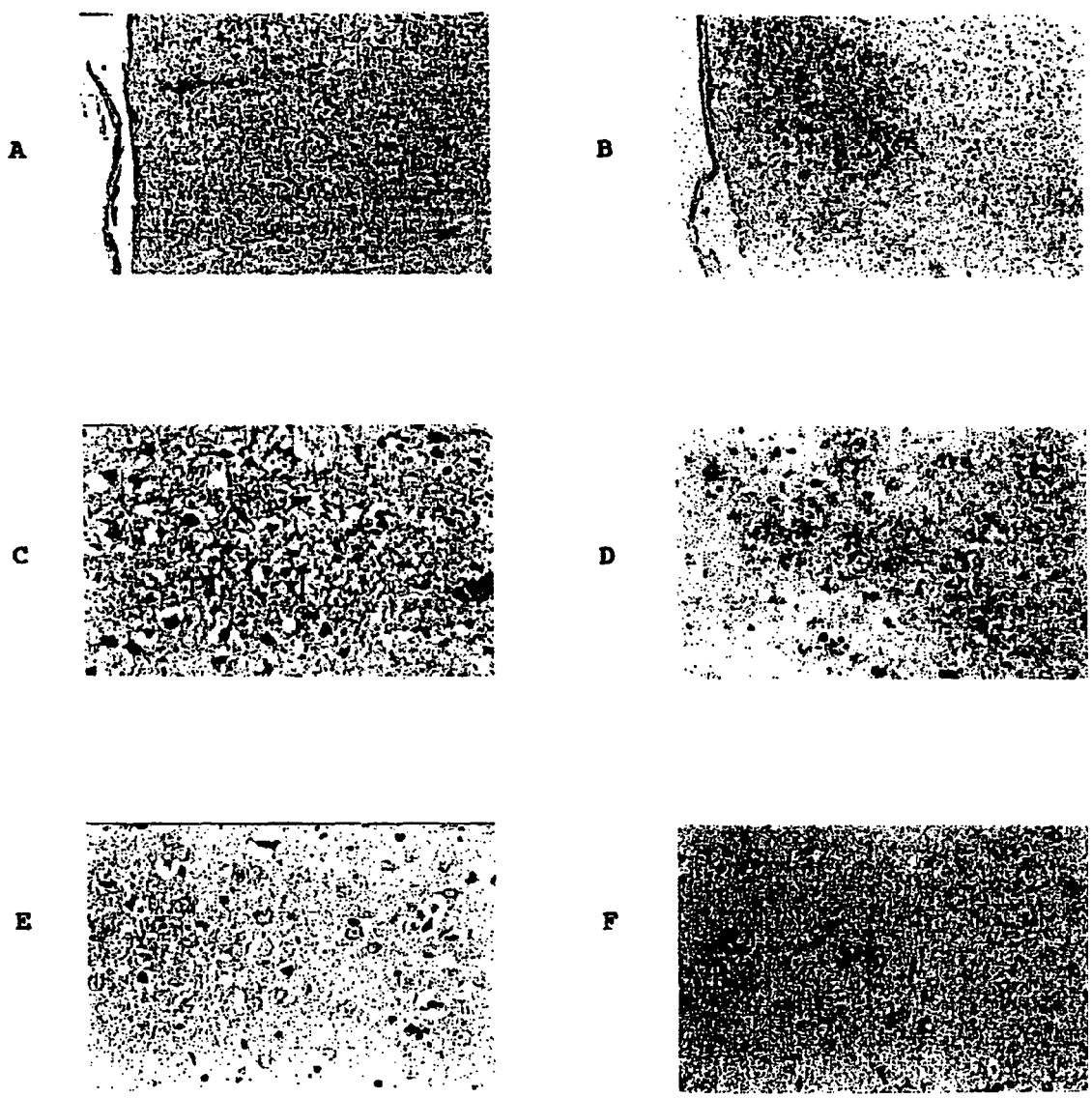
FIG. 3 presents photographs of brain cells from a head trauma model rat. A, C, and E are stained with H-E. B, D, and F are images corresponding to A, C and E stained with an anti-MK antibody. Magnifications are 25-fold for A and B, and 100-fold for C, D, E and F.

In Example 2, MK expression was examined in a model of cerebral infarction caused by ischemia. In this example, a model of infarction caused by mechanical stress was prepared to examine MK expression therein. Ten male SD rats (body weight, 320 g) were used. They were anesthetized by intraperitoneal injection of 4% chloral hydrate (10 ml/kg). The cerebral cortex was ablated to prepare a brain injury model. Scalp was incised with scissors, and a 4 mm diameter, 3 mm thick portion of the cerebral cortex was ablated at 3 mm toward the left eye along the coronal suture and a further 3 mm toward the occiput along the sagittal suture. A Dispopunch (disposable skin trepan) (Stiefel Laboratories) was used for ablation. After the complete ablation was confirmed, the scalp was sutured, and the animals were fed again with free access to water and food. On each of Days 1, 2, 4, 7, and 14 after the preparation of the brain injury model, 5 μm-thick slices were prepared from two rats in a similar manner as in Example 2. Their paraffin sections were prepared and stained with H.E and anti-mouse MK antibody. The results obtained on Day 1 after the preparation of the brain injury model are shown in FIG. 3; panels A, C and E present H-E staining, and panels B, D and F present anti-MK antibody staining. The panels confirm that MK reacts very quickly to mechanical injuries. Images A, C, and E of H-E stained tissues indicate that brain cells suffered from great damage by mechanical injuries. Images B, D, and F of the tissues stained with the anti-MK antibody show many cells positive to the antibody staining mainly near the hemorrhoidal area and in the area where brain cells were highly damaged, which corresponds to the area stained in A, C, and E. These results clearly demonstrate that, even in the case of neurocyte suffering from injury caused by both ischemic stress and mechanical stress, MK responds to the injury at the early stage and is expressed near the injured area.

Example 4

Expression of MK in Myocardial Infarction Model 4.1 Preparation of Myocardial Infarction Model An experimental myocardial infarction was prepared on the left ventricular wall of Wistar rats (7-week-old, male) according to the method of Fine, G. et al. (Fine, G., Morales, A. and Scerpella, J. R.: Arch. Path. 82: 4-8, 1966), by ligating the left anterior descending coronary artery (LAD). Six hours after the ligation, the rats were sacrificed, and the heart was immediately excised for analysis. In order to confirm the viability of myocardial cells (Fishbein, M. C. et al.: Am. Heart J. 101: 593-600, 1981), the inventors measured the area and size of myocardial infarction by staining with triphenyl tetrazolium chloride (TTC).

4.2 MK, Anti-MK Antibody, and Anti-bFGF Antibody

MK and an affinity-purified rabbit anti-mouse MK antibody were prepared according to the method of Take, M. et al. (Take, M. et al.: J. Biochem. 116: 1063-1068, 1994). The specificity of the affinity-purified anti-MK antibody was almost the same as that of the antibody described in Muramatsu et al. (Muramatsu, H. et al.: Dev. Biol. 159: 392-402, 1993). This antibody reacted with MK but not with PTN in the Western blot analysis. MAb52 (Wako Pure Chemicals) was used as the mouse anti-human bFGF monoclonal antibody. This antibody recognizes the rat bFGF (Takami, K. et al.: Exp. Brain Res. 90: 1-10, 1992).

4.3 Immunohistochemical Analysis

A horizontal cross section of the ventricular region of rat heart was taken out, fixed in a neutral buffer-formalin fixative at room temperature, embedded in paraffin, and cut into 5 μm-thick sections. After being deparaffinized, the sections were incubated in a 100% methanol containing 0.3% hydrogen peroxide solution for 30 min to block endogenous peroxidase. Bovine serum albumin (1%) was added to the sections, and the reaction was allowed to proceed for 30 min. In order to detect MK, these sections were incubated with the affinity-purified rabbit anti-MK polyclonal antibody (8 μg/ml) at 4° C. overnight. The sections were incubated with a biotinized goat anti-rabbit IgG antibody (Vector Laboratories Corp., California) for 30 min, and then with a biotinized alkaline phosphatase-streptavidin complex (Dako, Giostrup, Denmark) for 30 min. To detect bFGF, the sections were incubated with the mouse anti-bFGF monoclonal antibody (5 μg/ml) at 4° C. overnight, then with a biotinized rabbit anti-mouse antibody (Vector Laboratories Corp., California) for 30 min, and further with a biotinized alkaline phosphatase-streptavidin complex (Dako, Giostrup, Denmark) for 30 min. The immunoreaction was visualized with a Fast Red TR/Naphthol (Sigma, St. Louis, Mo.). Counterstaining was performed with hematoxylin. The specificity of MK immunostaining was determined by allowing recombinant MK to absorb the anti-MK antibody and subjecting the resulting complex to heparin-Sepharose affinity chromatography (Yasuhara, O. et al.: Biochem. Biophys. Res. Commun., 192: 246-251, 1993).

The results are shown in FIGS. 4 to 13.

Figure 4:
FIG. 4 is a photomicrograph showing the distribution of MK in a normal heart.
Figure 5:
FIG. 5 is a photomicrograph showing the distribution of MK in a normal heart.
Figure 6:
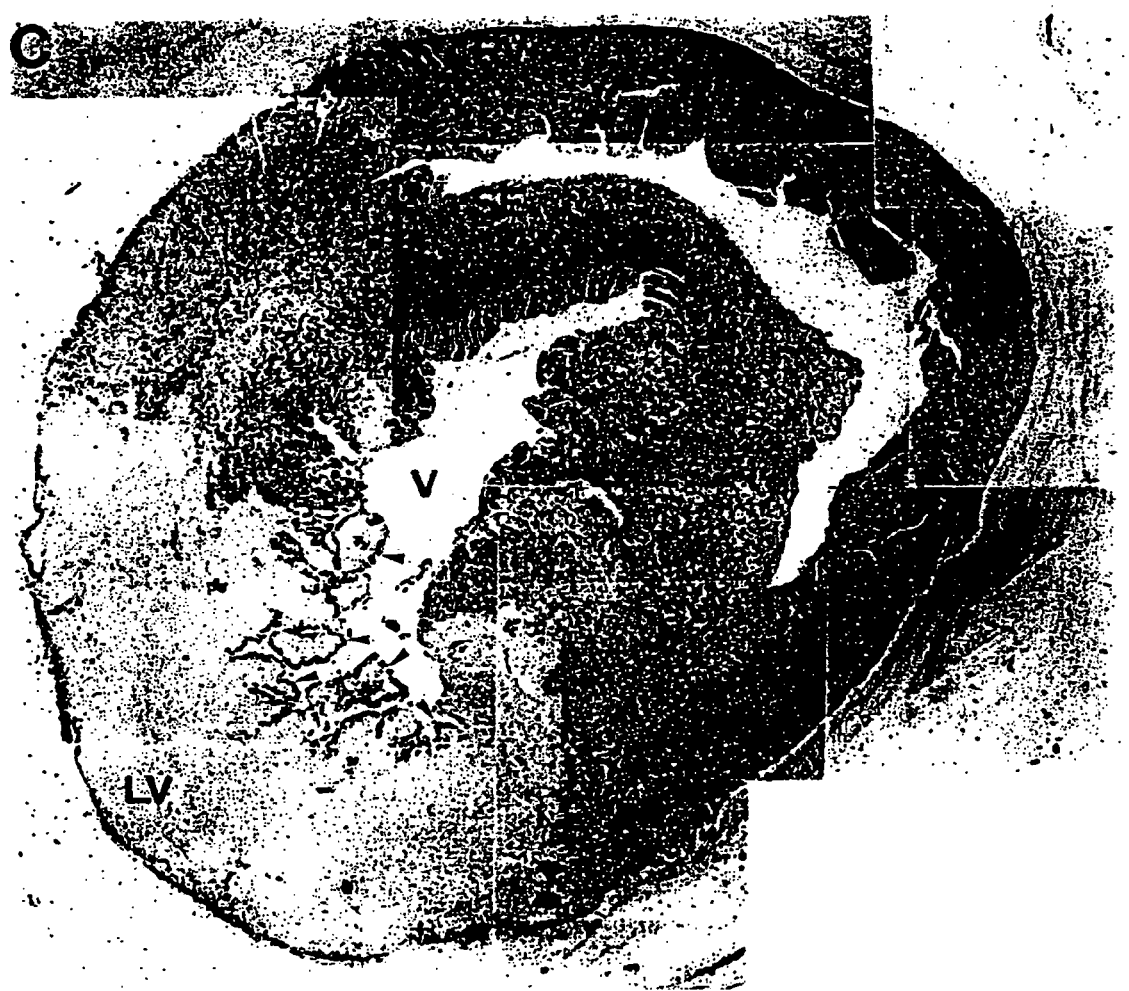
FIG. 6 is a photomicrograph showing the distribution of MK in a rat heart after the obstruction of the left anterior descending coronary artery.
Figure 7:
FIG. 7 is a photomicrograph showing the distribution of MK in a control of the rat heart after the obstruction of the left anterior descending coronary artery.
Figure 8:
FIG. 8 is a photomicrograph showing the distribution of MK on the right ventricular wall of a rat heart six hours after the formation of myocardial infarction.
Figure 9:
FIG. 9 is a photomicrograph showing the distribution of MK in the septum of a rat heart six hours after the formation of myocardial infarction.

FIGS. 4 to 7 are photomicrographs showing enhanced stainability of MK in rat heart after the occlusion of the left anterior descending coronary artery. FIGS. 4 and 5 represent a normal, immunohistochemically stained rat heart, in which MK is expressed in some myocardial cells facing the ventricle. A weak immunoreaction is detected in other myocardial cells of the septum. However, most of myocardial cells express almost no MK. FIG. 6 is a photomicrograph showing a rat heart six hours after the formation of myocardial infarction. Strong MK staining is detected in the septum (SE), the right ventricular wall (RV), and the endocardium (area indicated by an arrow) of the left ventricular wall (LV). The difference in the immunostaining between the left ventricular wall and the septum is very obvious. Stained and non-stained regions are divided by a single distinct border corresponding to the bordering region of each coronary artery that supplies nutrients to these regions. Myocardial cells in the cell death region of LV are not stained. The MK expression pattern observed in the heart having a infarcted site was different from that of bFGF in the same heart. FIG. 7 is a photomicrograph showing a control staining with a neutralizing anti-MK antibody. Since cells were not stained after treatment with the neutralizing anti-MK antibody, MR was confirmed to be stained specifically by this method. Bars shown in figures represent 1500 μm in FIGS. 4, 6 and 7, and 150 μm in FIG. 5.

Figure 10:
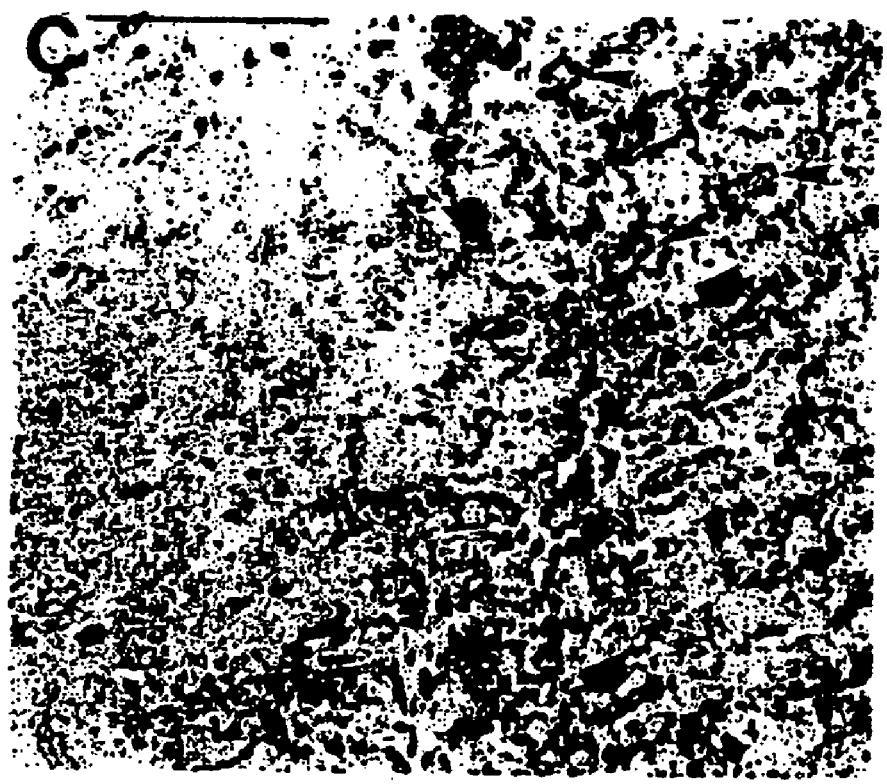
FIG. 10 is a photomicrograph showing the distribution of MK in the border region of the septum, and the ventricular wall and the left ventricular wall with the infarcted site of a rat heart six hours after the formation of myocardial infarction.
Figure 11:
FIG. 11 is a photomicrograph showing the distribution of MK in the septum of a rat heart six hours after the formation of myocardial infarction.
Figure 12:
FIG. 12 is a photomicrograph showing the distribution of MK in the left ventricular wall of a rat heart six hours after the formation of myocardial infarction.
Figure 13:
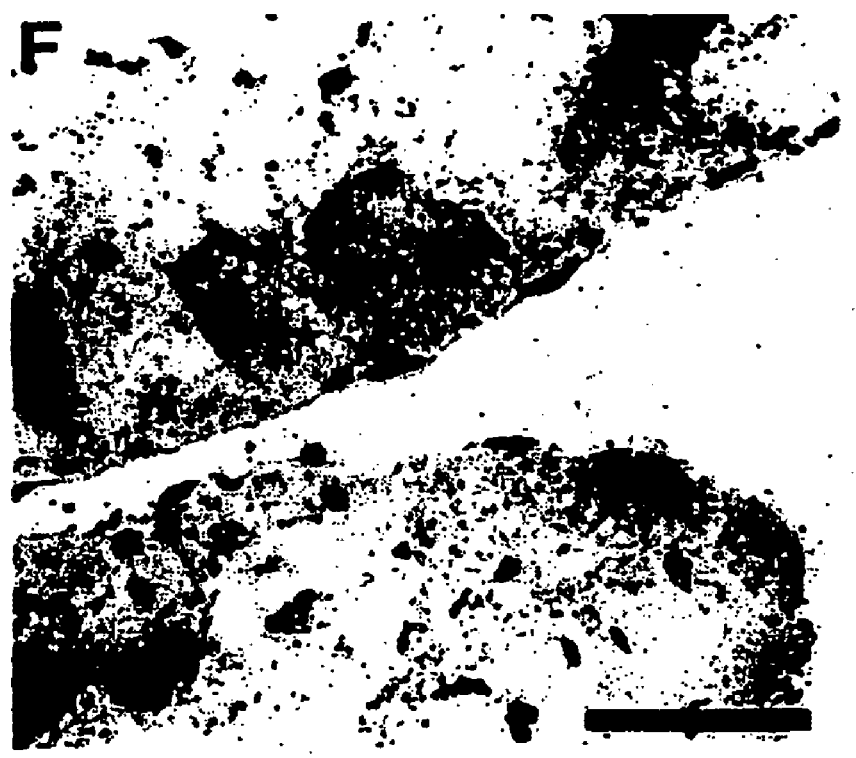
FIG. 13 is a photomicrograph showing the distribution of MK in the endocardium of the left ventricle of a rat heart six hours after the formation of myocardial infarction.

FIGS. 8 to 13 are photomicrographs showing the detailed MK expression in a rat heart six hours after the formation of myocardial infarction. Immunohistochemical staining of MK was detected in the right ventricular wall (FIG. 8), the septum (FIGS. 9 and 11), the border region between the septum, the ventricular wall having infarcted areas, and the left ventricular wall (FIG. 10), the left ventricular wall (FIG. 12), and the endocardium within the left ventricle (FIG. 13). Immunoreaction of MK was observed in myocardial cells (portions indicated with asterisks in FIGS. 11 and 13) and the penumbra of myocardial cells facing endothelial cells or endothelial cells themselves (portions indicated with an arrow and an arrowhead). In a high-magnification photomicrograph of the septum (FIG. 11), MK was intensely stained in the penumbra of myocardial cells facing the blood vessels or vascular endothelial cells. The inside of myocardial cells (FIG. 13) is also stained intensely or moderately (portions indicated with asterisks). The border between the septum and LV clearly separates non-stained and stained regions (FIG. 10). Bars shown in figures represent 200 μm in FIGS. 8, 9 and 10, and 50 μm in FIGS. 11, 12 and 13.

Example 5

Measurement of MK in Serum from Infraction Patient

Figure 14:
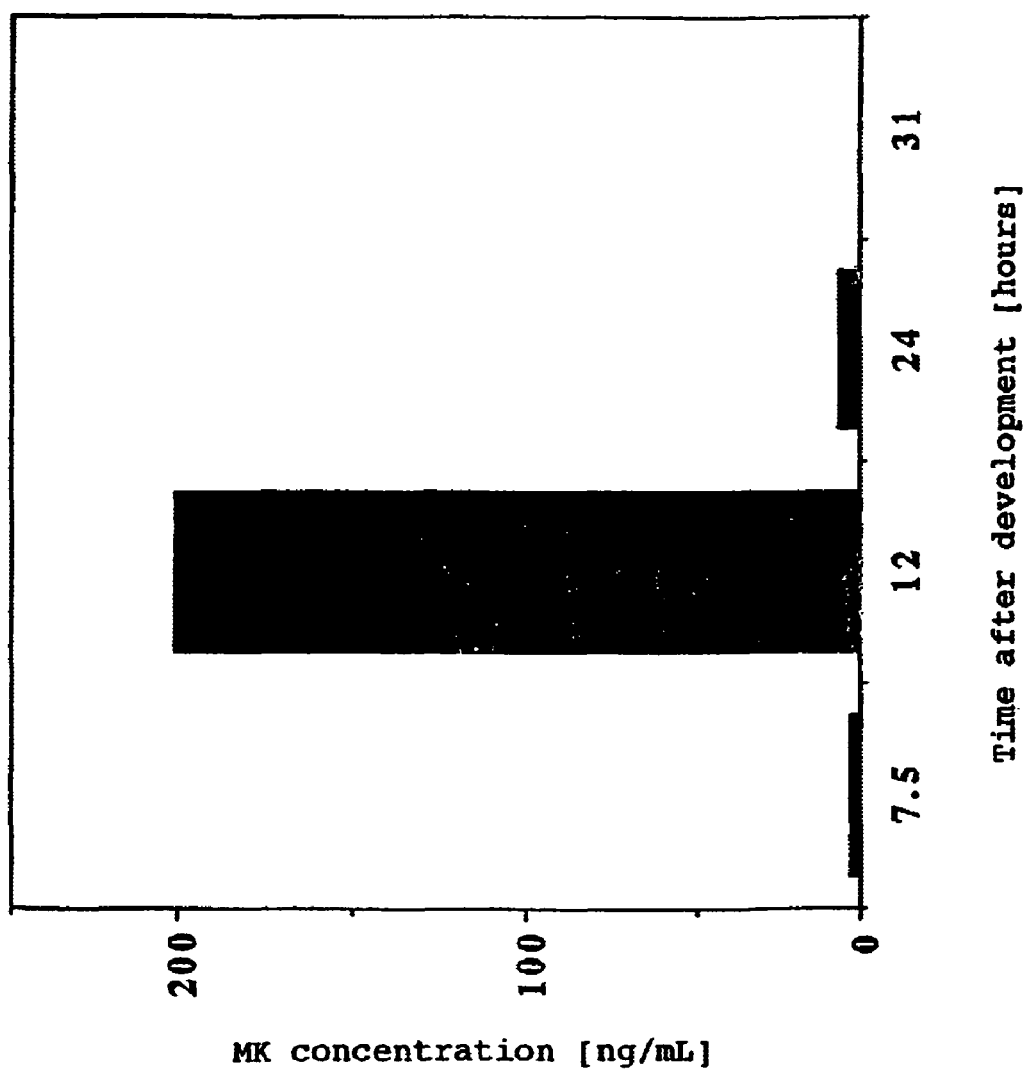
FIG. 14 is a graph showing the result of periodic measurement of MK concentration in serum from a myocardial infarction patient.
Figure 15:
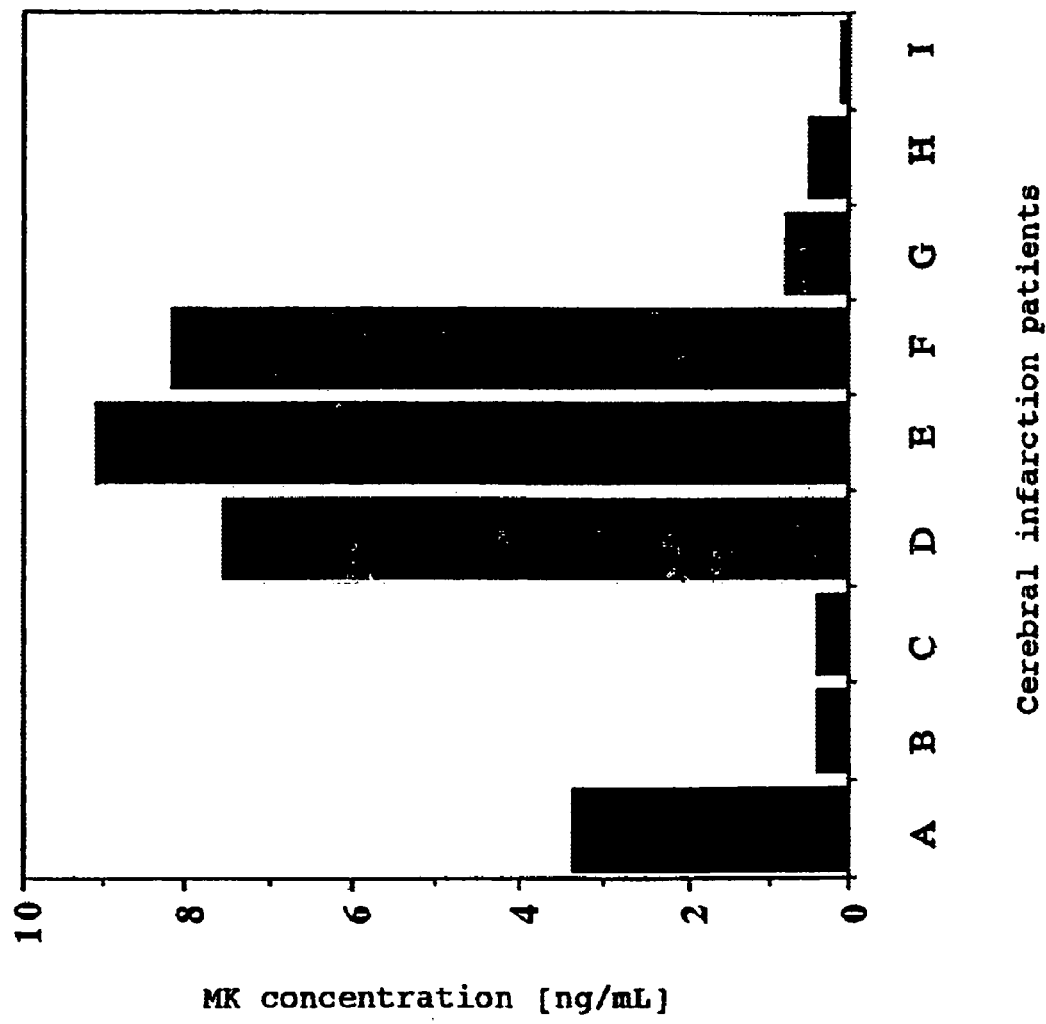
FIG. 15 is a graph showing the result of periodic measurement of MK concentration in serum from a cerebral infarction patient.

Using an EIA system described in JP-A Hei 10-160735, the inventors determined the MK concentration in sera from patients with myocardial infarction and cerebral infarction. Each serum sample collected from patients was centrifuged at 3,000 rpm for 15 min (at room temperature). These sera were stored at −80° C. FIG. 14 shows an example of the periodically determined MK concentration in serum from a patient with myocardial infarction. MK was expressed in the relatively early stage after development of myocardial infarction. Its concentration in blood increased and reached a peak 12 hours after the development. After 24 hours, it decreased to the same level as six hours after the development, and, after 31 hours, to about 0.16 ng/ml, which is the average level of normal subjects. This change in the MK concentration in blood after the development of myocardial infarction is probably unique to MK. Such a correlation of myocardial infarction with MK, including the MK expression in the infarctic penumbra at the early stage, indicates the involvement of MK in the repair mechanism of cardiac muscle. FIG. 15 shows the MK concentration in sera from cerebral infarction patients. In cerebral infarction cases also, MK was found in a very high concentration in blood from patients whose blood samples were thought to be collected at the early stage after the development of cerebral infarction such as in FIG. 15 A, D, E and F. These data are considered interesting in studying, at the individual level, the fact that a large amount of MK is detected near the area with cerebral infarction in an early stage after the development.

INDUSTRIAL APPLICABILITY

The midkine family proteins or partial peptides thereof according to this invention are efficacious in treating or preventing cytopathy caused by ischemia, or ischemic diseases due to said cytopathy. For example, these proteins are effective as medicaments for treating or preventing cerebrovascular disorders such as cerebrovascular spasm following subarachnoid hemorrhage, Alzheimer's disease, senile dementia of Alzheimer's type, cerebrovascular senile dementia, etc. as well as cerebral infarction, transient ischemic diseases, and head trauma, and other cerebrovascular diseases such as Parkinson's disease, Huntington's chorea, amyotrophic regressive disorders, etc. Furthermore, these proteins are expected to be used as medicaments for treating or preventing ischemic diseases such as myocardial infarction or angina of effort; ischemic colitis; superior mesenteric artery obstruction, etc.

In addition, these proteins can be expected to be used in gene therapy by activating promoters for genes of MK and PTN to express MK and PTN proteins in ischemic sites.

We claim:

1. A method for inhibiting delayed neurocyte death following transient cerebral ischemia, said method comprising administering to a subject at risk of suffering from a cerebral infarct or suffering from a transient cerebral ischemia a pharmaceutical composition consisting of a human or murine midkine protein and a pharmaceutically acceptable carrier at a dosage and by a route that permeates the blood-brain barrier and inhibits a delayed neurocyte death caused by apoptosis of ischemic neurocytes of an infarctic penumbra following the transient cerebral ischemia.

2. The method according to claim 1, wherein said administering of the pharmaceutical composition is before a cerebral infarct in the subject.

3. The method according to claim 1, wherein said administering of the pharmaceutical composition is after the transient cerebral ischemia and before delayed neurocyte cell death in brain of the subject.

4. The method according to claim 1, wherein the delayed neurocyte death comprises deciduation of neurons or denaturation of neurocytes in the infarctic penumbra following the transient cerebral ischemia.

5. The method according to claim 1, wherein said administering is by catheter.

6. The method according to claim 1, wherein said administering is by injection.

7. The method according to claim 1, further comprising administering to the subject one or more neurotrophic factors other than a midkine protein.

8. The method according to claim 1, wherein the transient cerebral ischemia is in brain parenchyma.

9. The method according to claim 1, wherein the transient cerebral ischemia is in a hippocampal CA1 area of brain.

10. The method according to claim 1, wherein the midkine protein is a human midkine protein.

11. The method according to claim 1, wherein the midkine protein is a mouse midkine protein.

* * * * *